United States Patent
Yu

(10) Patent No.: US 7,343,779 B1
(45) Date of Patent: Mar. 18, 2008

(54) HIGH PERFORMANCE, HAND-HELD GAS CHROMATOGRAPH, METHOD AND SYSTEM

(76) Inventor: Conrad M. Yu, 1920 Gateway Dr., Oakley, CA (US) 94561

( * ) Notice: Subject to any disclaimer, the term of this patent is extended or adjusted under 35 U.S.C. 154(b) by 231 days.

(21) Appl. No.: 11/295,233

(22) Filed: Dec. 5, 2005

(51) Int. Cl.
*G01N 30/06* (2006.01)
*G01N 30/26* (2006.01)
*G01N 30/62* (2006.01)

(52) U.S. Cl. ............... 73/23.41; 73/23.35; 73/23.4; 73/23.42; 95/82; 96/101; 96/102; 96/105; 422/89

(58) Field of Classification Search .......... 73/23.35, 73/23.39, 23.4, 23.41, 23.42; 96/101, 102, 96/105; 95/82, 87, 88, 89; 422/89; 436/161
See application file for complete search history.

(56) References Cited

U.S. PATENT DOCUMENTS

| | | | |
|---|---|---|---|
| 5,313,061 A | 5/1994 | Drew et al. | |
| 5,583,281 A | 12/1996 | Yu | |
| 5,719,322 A * | 2/1998 | Lansbarkis et al. | 73/23.39 |
| 6,306,200 B1 * | 10/2001 | Yu | 96/102 |
| 6,447,575 B2 | 9/2002 | Bremer et al. | |
| 6,457,347 B1 | 10/2002 | Koo et al. | |
| 6,490,852 B1 * | 12/2002 | Mustacich et al. | 57/3 |
| 6,627,454 B2 | 9/2003 | Amiriav et al. | |
| 6,653,144 B1 | 11/2003 | Nishina et al. | |
| 6,684,721 B2 | 2/2004 | Vanatta | |
| 6,719,826 B2 | 4/2004 | Sasano et al. | |
| 6,736,000 B2 | 5/2004 | Koo et al. | |
| 2004/0056016 A1 * | 3/2004 | Tian et al. | 219/408 |

OTHER PUBLICATIONS

Yu, C.M. et al., "A High Performance Hand-Held Gas Chromatograph", U.S. Department of Energy, Lawrence Livermore National Laboratory, UCRL-JC-130439-REV-1, Jan. 10, 2001.*
S. C. Terry, J.H. Jerman, and J.B. Angell, "A gas chromatograph air analyzer fabricated on a silicon wafer." IEEE Trans. Electron devices, vol. ED-26, p. 1880 (1979).
W. Kern, "Chemical etching of silicon, germanium, gallium arsenide, and gallium phosphide," RCA Rev., vol. 29, p. 278, no year/date.
A. Manz, et al. (Hitachi, Japan), "Design of an open-tubular column liquid chromatography using silicon chip technology." Sensors and Actuators, B1 (1990), pp. 249-255.
R. Reston and E. Kolesar, "Silicon-micromachined gas chromatography system . . . " J. of Microelectromechanical Systems, vol. 3, No. 4 (1994) pp. 134-146.

* cited by examiner

*Primary Examiner*—Daniel S. Larkin
(74) *Attorney, Agent, or Firm*—Charles L. Thoeming

(57) ABSTRACT

A hand-held, ultra-sensitive gas chromatograph which provides real time detection and analysis of chemical compounds or impurities is disclosed. The detection sensitivity ranges from parts per trillion to parts per million with an average retention time ranging from thirty to forty-five seconds. Optimum calculated effective plate number is 55,000, with a response time on the order of two minutes. The self-contained apparatus operates on twenty-four watts, weighs twelve pounds, and measures 8"×6"×13."

52 Claims, 17 Drawing Sheets

HIGH PERFORMANCE, HAND-HELD GAS CHROMATOGRAPH, METHOD AND SYSTEM

CROSS-REFERENCES TO RELATED APPLICATIONS

None.

STATEMENT REGARDING FEDERALLY SPONSORED RESEARCH OR DEVELOPMENT

None.

REFERENCE TO A MICRO-FICHE APPENDIX

None.

TECHNICAL FIELD

The present invention relates to gas chromatography, and more particularly to a portable, hand-held gas chromatograph, and system and method for the same, capable of accelerated real time analysis and highly sensitive measurements suitable for a broad range of scientific, commercial, military, and homeland security applications.

BACKGROUND OF THE INVENTION

A search of the prior art located the following United States patents which are believed to be representative of the present state of the prior art: U.S. Pat. No. 5,313,061, issued May 17, 1994; U.S. Pat. No. 6,627,454, issued Sep. 30, 2003; U.S. Pat. No. 6,653,144, issued Nov. 25, 2003; U.S. Pat. No. 6,684,721, issued Feb. 3, 2004; U.S. Pat. No. 6,719,826, issued Apr. 13, 2004; U.S. Pat. No. 6,447,575, issued Sep. 10, 2002; U.S. Pat. No. 6,736,000, issued May 18, 2004; U.S. Pat. No. 6,457,347, issued Oct. 1, 2002; and U.S. Pat. No. 5,583,281, issued Dec. 10, 1996.

DISCLOSURE OF INVENTION

Gas chromatography is a prominent technique for separating complex gasses and then analyzing the relative quantities of each of the separate components in the blend. This analytical technique has gained popularity over a broad range of applications, including monitoring environmental parameters for air and water quality, and chemical and biological analysis. Advances in the art underscore the need to move gas chromatography analysis away from the laboratory and to the point of origin for the sample. This need necessarily requires chromatography systems and methods, which combine faster real time data collection and lower analysis costs.

In gas chromatography, an unknown chemical mixture is first injected and pushed by a carrier gas into its separation column. In the separation column the chemical mixture is distributed between two phases, a mobile phase and a stationary phase. A carrier gas in the separation column transports the mobile phase. The stationary phase is adsorbed and desorbed into a solid. Based upon the kinetics of the adsorption-desorption process in the gas-solid interface of the column, different chemicals achieve different moving speeds in the carrier gas. Within a precise column length, the chemical mixture can be separated into various components and recorded by a detector. Conventional gas chromatographs provide detector sensitivities in the parts per million for thermal sensitivity detectors and parts per billion for various ion cell detectors. Chemical components are identified through their retention times and the traverse time for each of them as they pass through the separation column.

In testing the composition of air, water, hazardous chemicals and other environmental as well as non-environmental samples, including the detection of drugs or explosives, it is necessary and desirable to conduct the tests at the point source or location of the materials. Often the materials are found outside of controlled environments providing power sources. Since, in exigent circumstances presented by drug or explosive materials, it is desirable to quickly ascertain the presence of such materials in a rapid manner in the absence of power sources available in controlled laboratory settings. There is a need for a hand-held, extremely sensitive instrument for testing or monitoring the chemical composition of such materials.

It is an objective of the present invention to provide a hand-held, real time detection gas chromatograph with a response time less than two minutes.

It is a further objective of the present invention to provide a hand-held, self-contained gas chromatograph with a calculated effective plate number of at least 50,000.

It is yet a further objective of the present invention to provide a hand-held, real time detection gas chromatograph with a detection sensitivity of parts per billion.

It is another objective of the present invention to provide a hand-held, real time detection gas chromatograph which can be efficiently and economically manufactured and used.

It is another objective of the present invention to provide a hand-held, real time detection gas chromatograph which can be remotely controlled and/or monitored using present technologies.

The present invention for a hand-held, real time detection gas chromatograph, system and method of use therefore provides a hand-held gas chromatograph apparatus weighing approximately twelve pounds within a 624 cubic inch volume without the necessity of micro-electro-mechanical-system ("MEMS") based components. The hand-held, self-contained gas chromatograph of an embodiment of the present invention requires approximately twenty-four watts of electrical power and has an effective response time on the order of two minutes. The glow discharge detector of an embodiment of the present invention provides sensitivity ranging from parts per trillion to parts per million with output measurements delivered in Gaussian peaks. The average retention time of an embodiment of the present invention is approximately thirty to forty-five seconds. Under optimum operating conditions the calculated effective plate number of an embodiment of the present invention is a least 50,000.

Other features, advantages, and objects of the present invention will become apparent with reference to the following detailed description and accompanying figures.

BEST MODE FOR CARRYING OUT THE INVENTION

Gas chromatography is a separation method in which the components of a sample partition between two phases. One of these phases is a stationary bed with a large surface area. The other is a gas which percolates through the stationary bed. The sample is vaporized or a gas sample, and is carried by the mobile gas phase (the carrier gas) through the column. Samples partition (equilibrate) into the stationary phase based upon their solubilities at the given temperature. The detector senses the effluents from the column and provides a record of the chromatography in the form of a chromatogram. The detector signals are proportionate to the quantity of each solute (analyte).

Figure 1A:
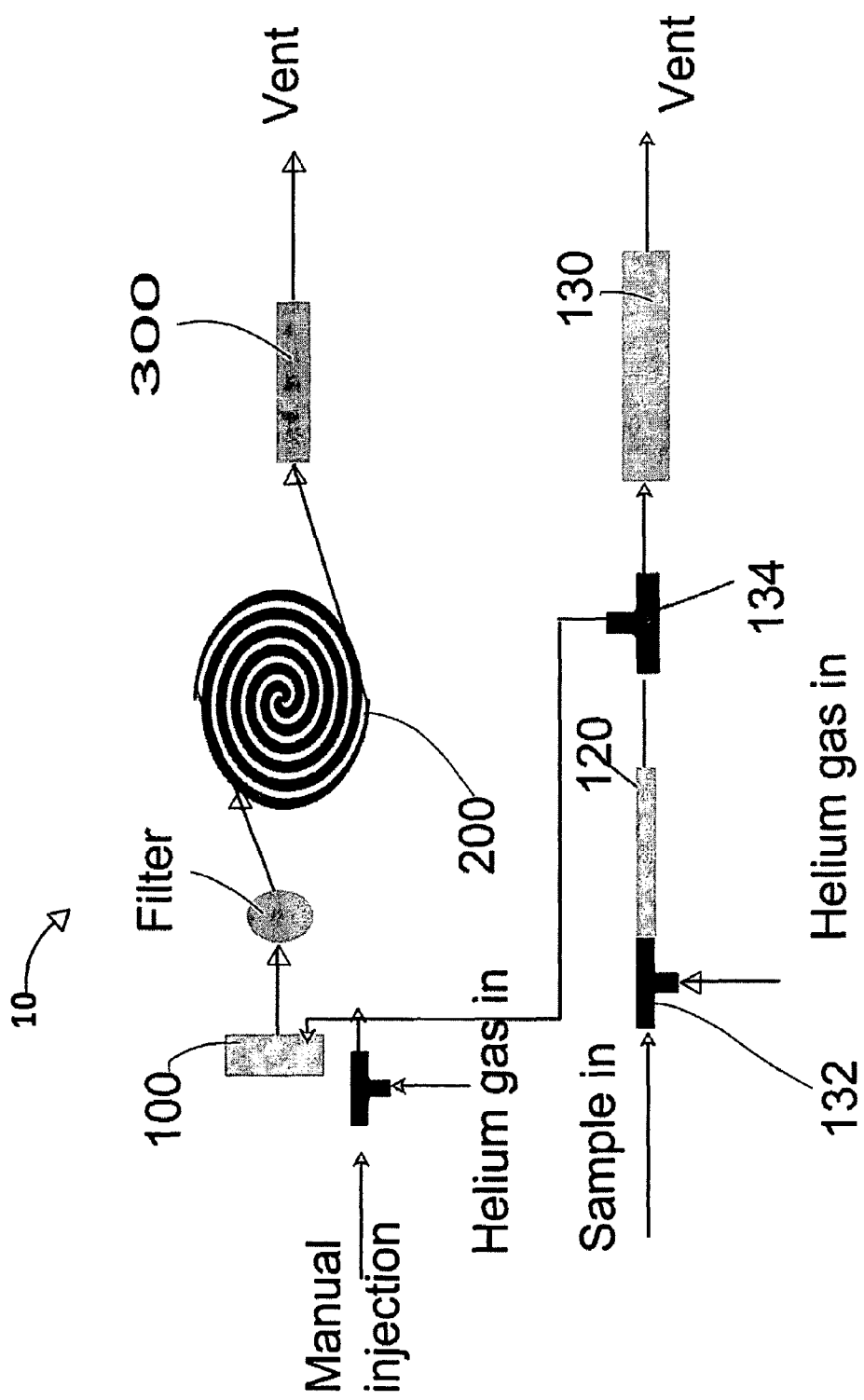
FIG. 1A is a block diagram illustrating the general elements of an embodiment of the present invention for a portable gas chromatograph.
Figure 1B:
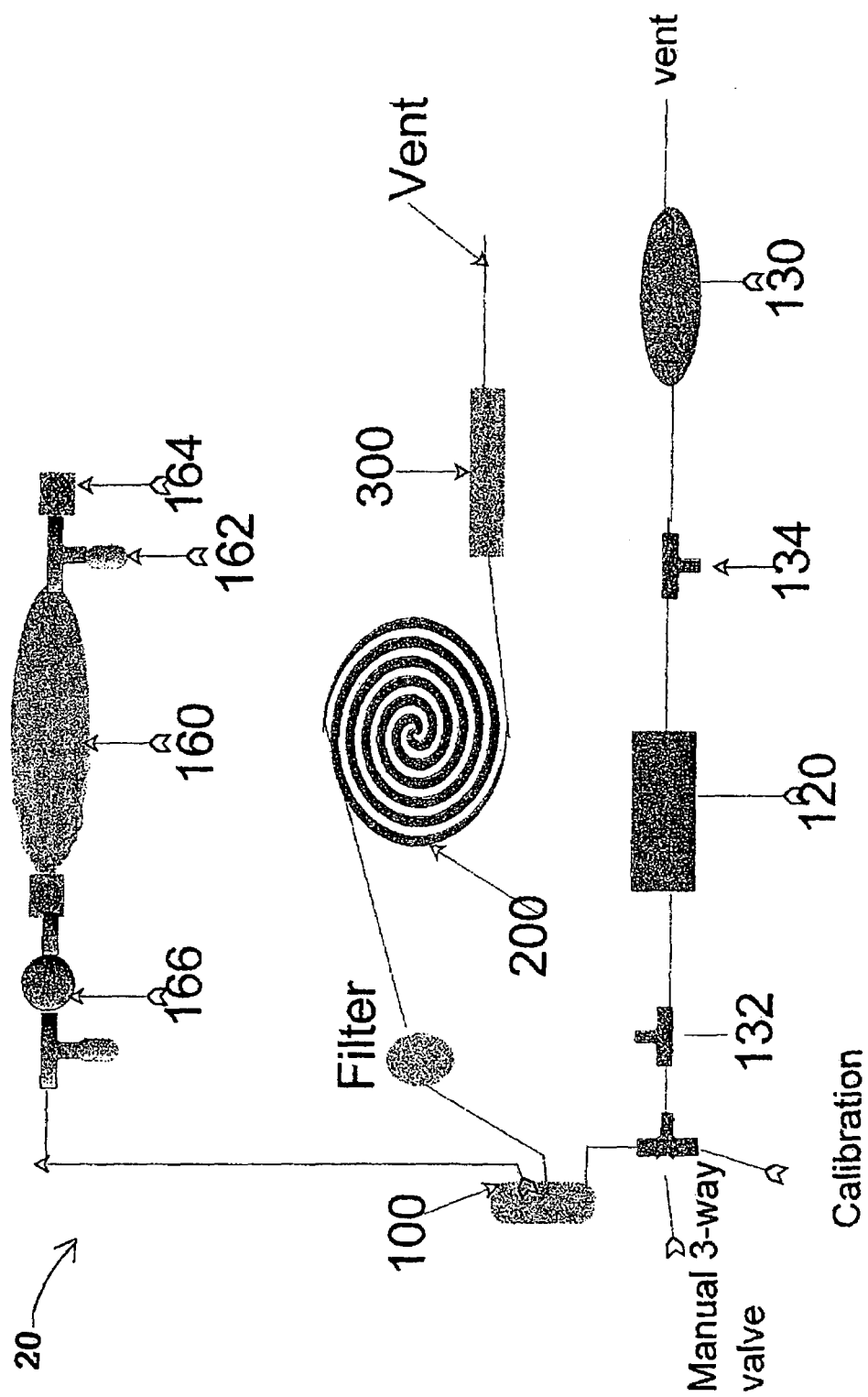
FIG. 1B is a block diagram illustrating the general elements of an embodiment of the present invention for a portable gas chromatograph.

With reference to the drawings, an embodiment of the present invention for a hand-held, real time detection gas chromatograph, system, and method of use is illustrated generally in the block diagrams of FIGS. 1A and 1B by the reference numerals 10 and 20, respectively. The principal components of the present invention for the gas chromatograph are self contained and comprise a sample injector 100 consisting of an eight-port valve, such as those manufactured by Valco Instruments Company, Inc. ("VICI"), a capillary separation column 200, and a glow discharge detector 300.

Figure 2:
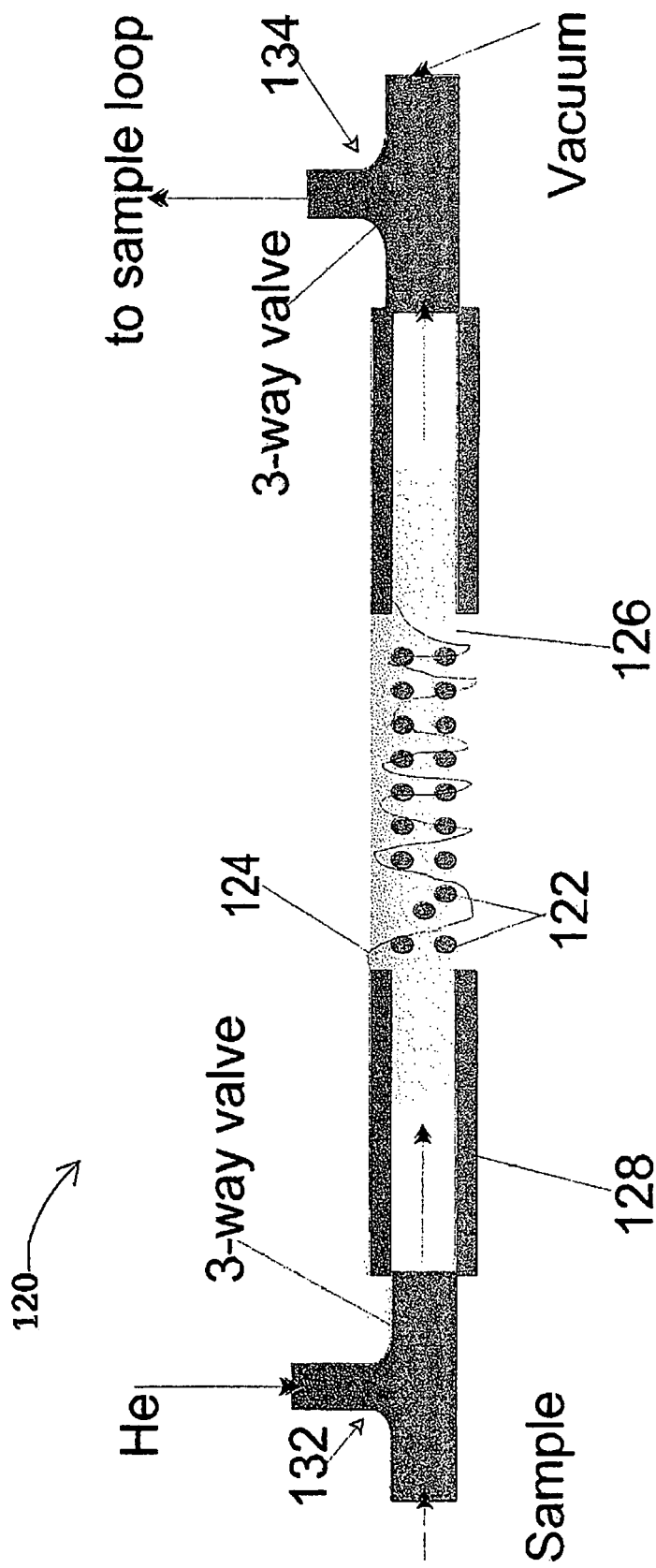
FIG. 2 is a cross sectional view of the sample pre-concentrator in the hand-held, real time detection gas chromatograph of FIGS. 1A and 1B.
Figure 3:
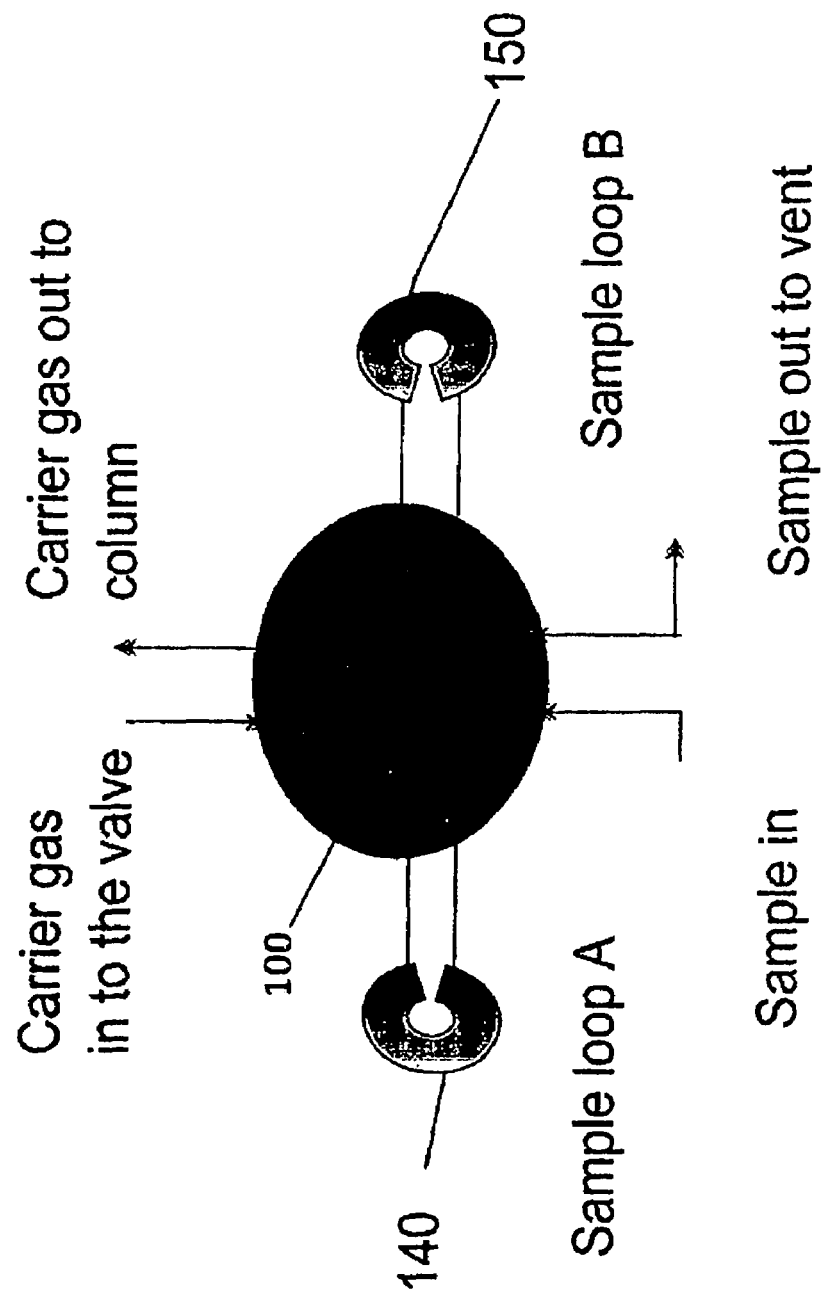
FIG. 3 is a flow diagram of an injector and its sample loop of the sample pre-concentrator in the hand-held, real time detection gas chromatograph of FIG. 2.
Figure 3A:
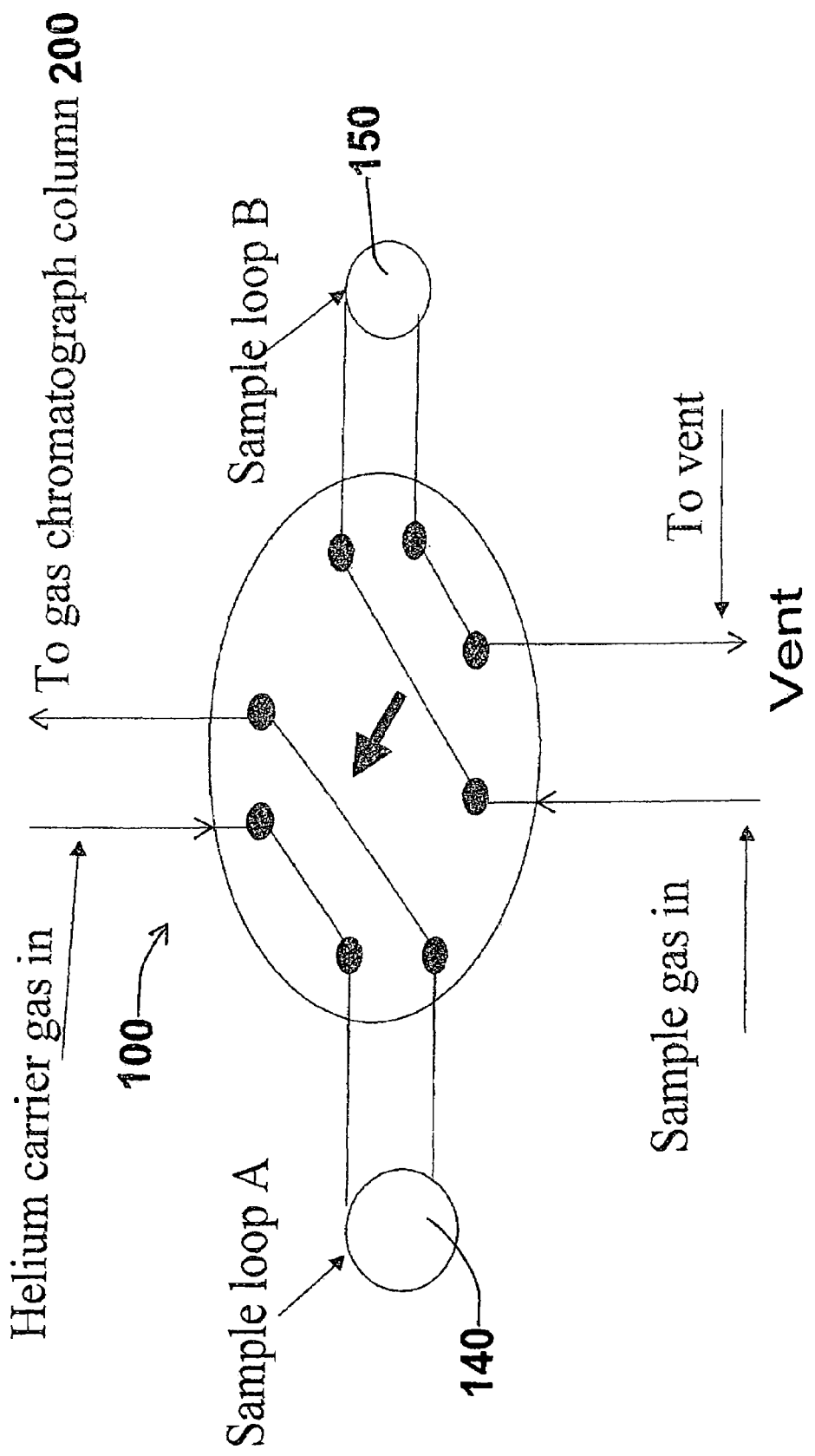
FIG. 3A is a flow diagram of an injector and its sample loop of the sample pre-concentrator in valve position A for the hand-held, real time detection gas chromatograph of FIG. 2.
Figure 3B:
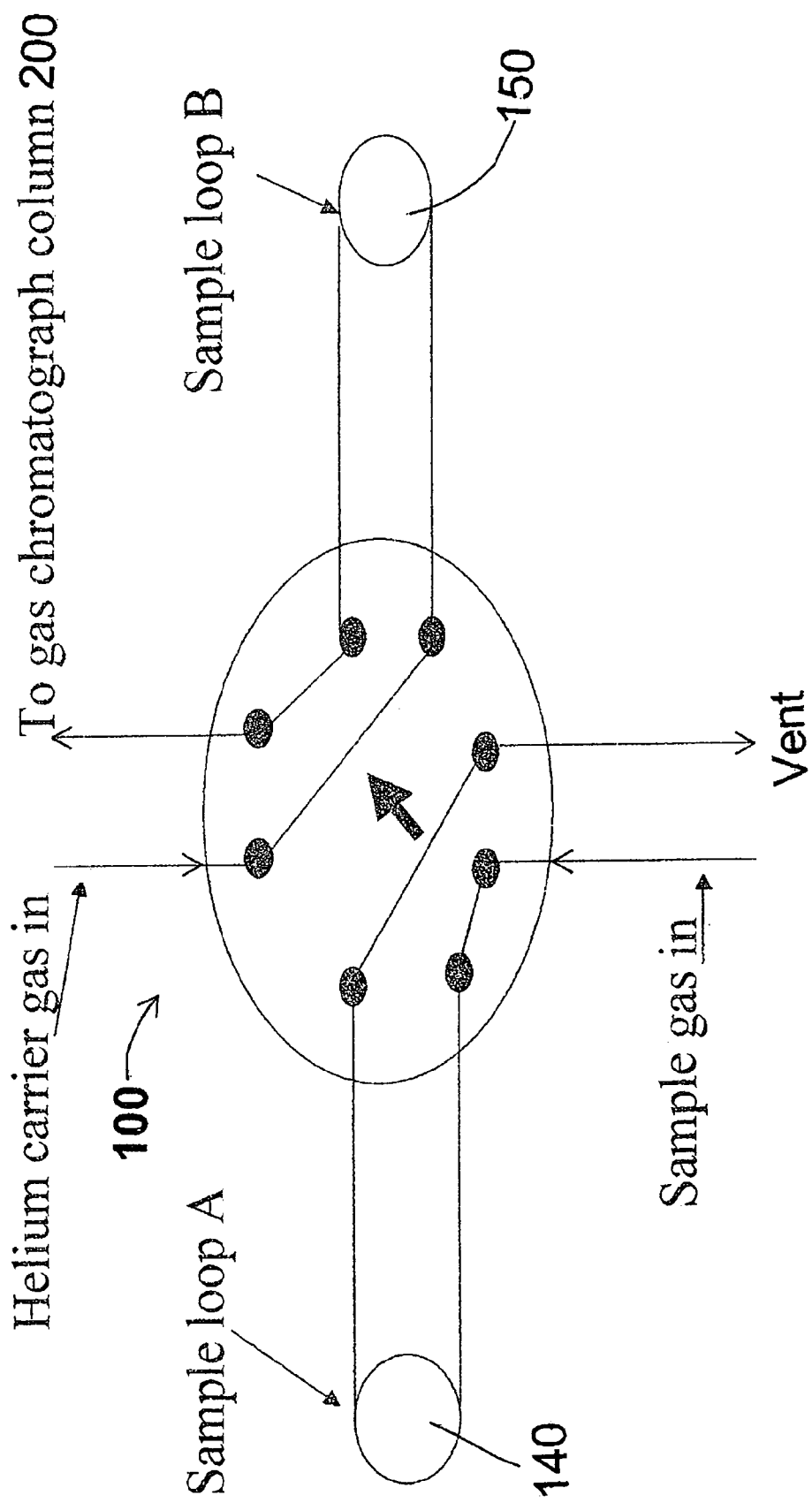
FIG. 3B is a flow diagram of an injector and its sample loop of the sample pre-concentrator in valve position B for the hand-held, real time detection gas chromatograph of FIG. 2.

The sample injector 100 of an embodiment of the present invention 10, FIGS. 1A, 1B, and 2, includes a pre-concentrator 120 comprising a non-conductive getter 122 and a resistance heater 124 housed within glass tubing 126 as the front end for the capillary separation column 200. As further illustrated in FIG. 2, the glass tubing is housed within stainless steel tubing 128. A small vacuum pump 130 pulls a precise amount of sample into the pre-concentrator 120, FIGS. 1A, 2, and 3. Two three-way valves, 132 and 134, switch from a normally open position to a redirected position. The sample pre-concentrator 120 activates to release the adsorbed sample to the carrier gas stream, and then transfers the stream into a first sample loop 140. After the sample has been injected into the column 200, the sample stream fills a second sample loop 150. Input to the present invention for gaseous sampling and analysis can include use of sniffer apparatus commonly used in the art. The present invention can likewise be used for liquid sampling and analysis.

An inert carrier gas is suitable for the mobile phase of the apparatus, system, and method of the present invention, usually nitrogen, hydrogen, helium, or argon. The preferred embodiment of the present invention uses helium as the carrier gas.

FIG. 1B illustrates an embodiment of the present invention 20 comprising a pressurized carrier gas reservoir 160. The flow from and to the reservoir 160 is controlled by a pressure sensor 162, a high to low pressure regulator 166, and a shut off valve 164. Flow of carrier gas from the reservoir to the heated injector 100 is controlled by the high to low pressure regulator 166.

The separation efficiency of the capillary separation column 200 is related to the degree to which a solute band broadens (which is a function of the width of the peak, w) relative to the length of time the band requires to traverse the column (its retention time tR), the number of theoretical plates n is defined as:

$$n=16(t_R/w)^2 \quad (1)$$

Or, the number of effective theoretical plates is defined as, $$N=5.56[(t_R-t_M)/w_{1/2}]^2 \quad (2)$$

where $t_M$ is the duration for non-absorbed gases to traverse the separation column and $w_{1/2}$ the half line-width of a signal peak. The efficiency of a separation column is measured by the number of theoretical plates per unit length or the "height equivalent to a theoretical plate" h (HETP), $$h=L/n \quad (3)$$

where, L is the total length of the separation column. Or, the "height equivalent to one effective theoretical plate" H (HEETP), $$H=L/N \quad (4)$$

The hand-held, real time gas chromatograph of the present invention should have a wide appeal for numerous applications, such as on-site real time toxic gas monitors, pollution detectors, reaction gas analysis, and law enforcement usage, especially useful for Home Land Security applications.

To insure high detection sensitivity, an improved glow discharge detector 300 has been developed. In the improved glow discharge detector 300, operational voltage in all practical cases is a constant. Because of high conductivity in the plasma region, operational voltage V(p) mainly equals the voltage-drop in the cathode dark region. Its operational current is locked by an external resistor. Therefore, it is also a constant. From Fowler and Nordheim's Equation of Field Emission, the electric field E on the surface S of the cathode should also be a constant so is its charge density on the surface of the cathode. They are related and can be expressed as, $$\epsilon_o E = \sigma \quad (5),$$

where, $\sigma$ is the surface charge density. This electric field E in the glow discharge is caused by the surrounding positive ions and the external applied electric field.

As a gas mixture passes through the gas chromatograph column 200, it separates into different sample plugs in the carrier gas. As these sample plugs pass sequentially through the glow discharge detector 300 some of their molecules are ionized. Depending upon their molecular ionization potential and the design of the glow discharge detector, these ions from the trace elements exist at different distances and locations on the surface of the cathode. In that duration, the surface electric field on the cathode is modified. In a glow discharge detector, it can be written as, $$I = I(O) * \{1(+/-)[E^2/E(0)] * \exp[-6.83 * 10^{\wedge}(9) * \phi''^{\wedge}(3/2) * v(y)/(\delta E)]\} \quad (6),$$

where I(O) is the original current, E the electrical field on the surface of the cathode, E(O) the original electrical field before the sample plug, $\phi''$ is the average work-function related to both ions, v(y) Nordheim elliptic function and the $\delta E$ is added field due to sample's ions. The v(y) is normally close to value of 1. With a proper designed glow discharge detector, all positive ions of the trace elements will be located behind the helium ions to cause the electrical field on the surface of the cathode to increase. From the equation (6), only the positive sign will apply. The electrical current will increase and thus reduces its operational voltage or vice versa. However, as the operational voltage decreases, the cathode dark region decreases. The distance between the ions and the cathode decreases. Depending upon the structure of cathode, the electric field on the surface of cathode will further increase. Since under ambient condition this distance between ions and surface of cathode is in the order of few tens or hundreds angstroms; it is relatively small than the area of surface, the relation of parallel plate electrodes can be used.

One can show, $$\rho = (1/V) * (\delta E)^2 = (1/V) * [1/\ln(\text{signal voltage})]^2 \quad (7),$$

where $\rho$ is the sample concentration. Because the electric current is exponentially related to the surface electric field on the cathode, the improved glow discharge detector 300 is highly sensitive and with a large dynamic range. Experiments using the preferred embodiment of the present invention have shown that it can detect normal hydrocarbons in parts per billion and for electron-capture-chemicals, parts per trillion or more.

Figure 4:
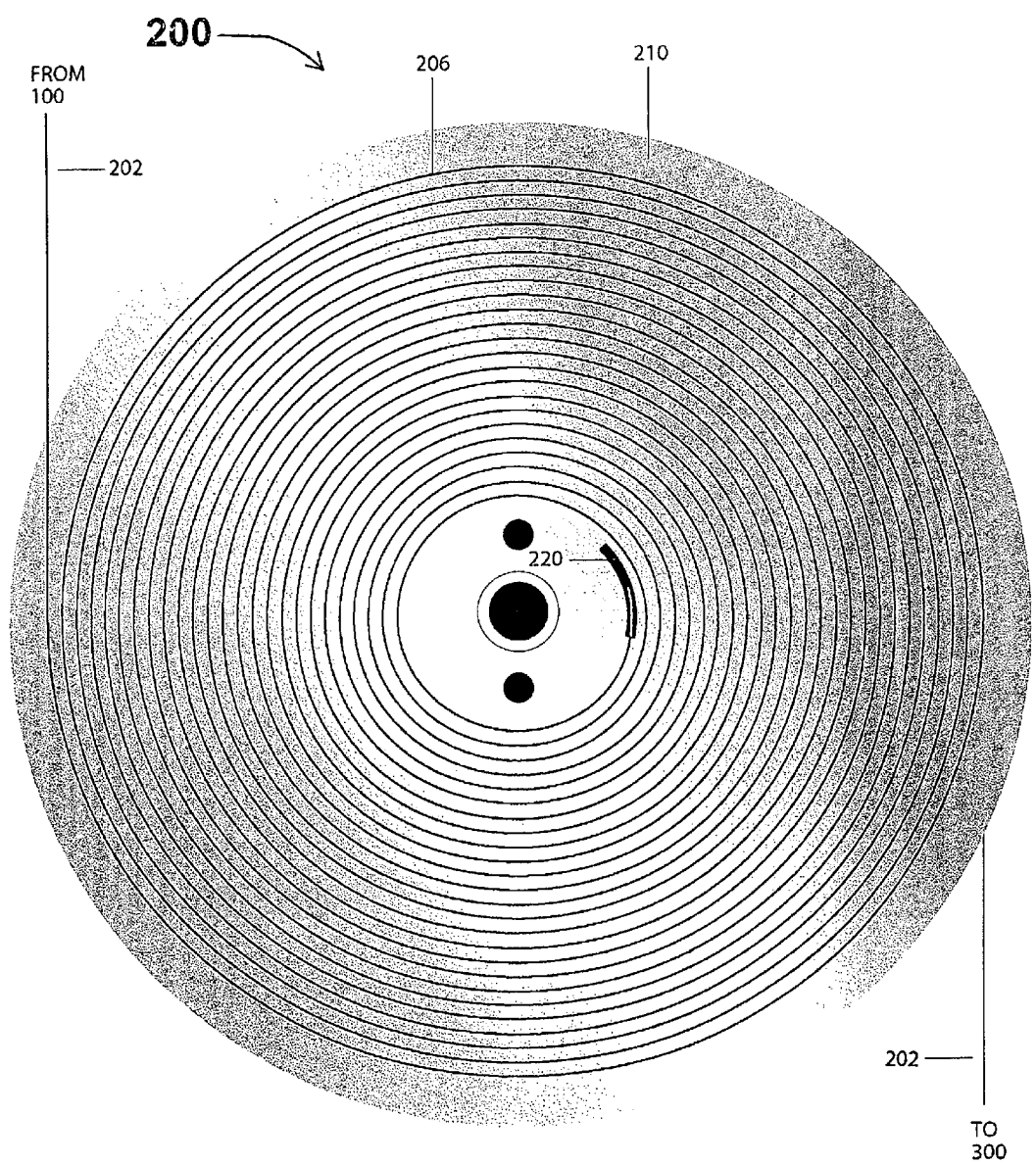
FIG. 4 is a top side view of a capillary separation column in the hand-held, real time detection gas chromatograph of FIGS. 1A and 1B.

Conventional gas chromatograph columns are typically twenty to fifty meters long with inside diameters of 250 to 350 microns. An embodiment of the present invention uses an inside diameter of one hundred microns and a five meter length. As illustrated in FIG. 4, the column 200 of an embodiment of the present invention is a capillary tubing 202 equipped with a heat exchanger and housed in a continuous 360 micron grooved channel 206 on both sides of an aluminum disk 210. The separation column 200 and its column oven are engineered in one package in the portable gas chromatograph. Aluminum is a good thermal conductor and provides rapid heating and cooling of the column. The portable gas chromatograph system of the present invention is capable of rapid column temperature ramping and cooling operations. These dynamic temperature operational features are especially important for organic and biological analyses in a variety of portable gas chromatograph applications.

The grooved channel spirals from the sample injector 100 to the outer edge of one side of the disk 210 towards an opening in the disk center 220. The capillary tubing 202 housed in the channel passes through the disk 210 and spirals from the center to exit the other disk side outer edge to the glow discharge detector 300. The length of the entire aluminum disk groove channel is 6.5 meters. High-grade aluminum metals are suitable materials for constructing the heat exchange element for the capillary tubing 202. The capillary tubing 202 of the preferred embodiment of the present invention is silica.

A high temperature conductive paste covers the column and grooved channels for optimal heat transfer. A resistant flat heater is firmly attached to the disk to provide rapid heating. Rapid column cooling is provided by convection from a fan blowing cool air across the disk. The operation temperature of separation column 200 of this embodiment of the present invention is as high as 350 degrees Celsius. The small mass of the system and apparatus of the present invention is capable of rapid column temperature ramping and cooling methods, which are especially important for organic and biological analysis in gas chromatograph applications.

By combining the characteristics of two separate effects due to negative electrons on the internal resistance and positive ions on the voltage drop in the dark space of the ionized trace elements in a simple glow discharge, the present invention provides a highly sensitive, improved glow discharge detector to detect trace elements in a gas flow.

Using constant current (DC) glow discharge in detection of trace elements in helium carrier gas of gas chromatography has been practiced for some time. In the art, this effect was concluded to be due to changing of conductivity in the glow discharge by additional ionization of trace elements. However, there was no detailed discussion of this effect, and no optimization process was presented. The electrical field effect of a pseudo-electrode near the cathode electrode was discussed and used in detection of trace elements in U.S. Pat. Nos. 6,457,347 and 6,736,000. In these latter cases, the constant electrical field construction is essential. However, they did not point out the difference between this version and the earlier version glow discharge detectors and whether or not the two could be combined in creating more sensitive glow discharge detectors. The present invention discloses these two versions of glow discharge detectors. The design of glow discharge detectors optimized in their detection sensitivity is described. It should be noted that glow discharge detectors of embodiments of the present invention are not limited in using helium as carrier gas; however, the preferred embodiment uses helium.

Figure 6:
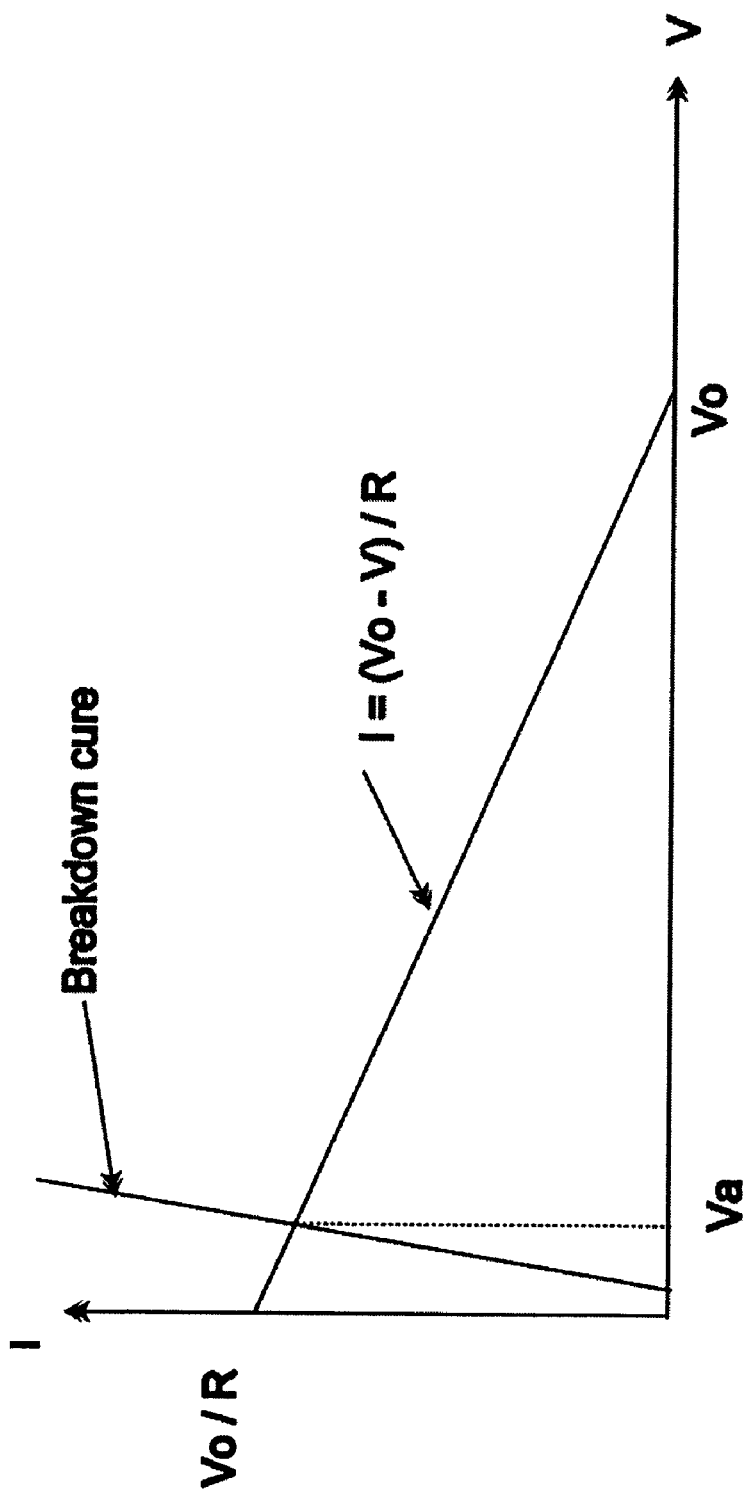
FIG. 6 is a graph depicting the solution to the equation $V_a=V_o-IR$ representing the inter-section of the voltage-current curve of the glow discharge and the straight line plot of the right side of the equation for the glow discharge detector of FIG. 5.

The phenomenon of DC glow discharge likewise is well known. It is composed of two electrodes. A cathode is connected to a negative external voltage. An anode is connected to a positive external voltage. As external voltage increases, an electrical field between the two electrodes increases. Electrons are emitted from the cathode electrode. This field emission is governed by the general principles set forth in Fowler and Nordheim: Equation of Field Emission. As external voltage increases further, the emitted electrons gain enough energy and start to ionize its surrounding gas molecules. The positive ions of gas molecules near the cathode form a positive pseudo-electrode and generate a strong electrical field near the cathode 302, FIG. 5A. More electrons with higher energy are emitted from the cathode 302 and cause more gas molecules to be ionized. The system starts to avalanche breakdown. In order to prevent the avalanche breakdown and to limit the electrical current to a reasonable value for glow discharge, a large resistor is normally incorporated in the circuit, FIG. 8. As further illustrated in FIG. 5A, in a glow discharge 800, the space between the cathode 302 and the pseudo-electrode of positive gas ions is called dark space, because there is no re-combination of the positive ions; no light is emitted in this region. Electrical glow exists only in the region between the pseudo-electrode and the anode 304, FIG. 5. The voltage relative to the glow discharge can be written as, $$V_a = V_o - IR \quad (9),$$

where $V_a$ is the voltage-drop cross the dark space, $V_o$ the external applied voltage, I the electrical current and R the total resistance in the circuit. This equation can be solved by diagram. $V_a$ is found by the inter-crossing between the voltage-current curve of the glow discharge and the straight line representing the right hand side of the equation, (where current I is the variable), as shown in FIG. 6.

In different gas environments, the voltage drop $V_a$ through the dark space is different. Among all gases, helium has smallest cross section and highest ionization energy. Therefore, it has the smallest voltage drop $V_a$ across its dark space. The value $V_a$ for helium is about 300 volts; for nitrogen or hydrogen is about 1000 volts. Since a minimal number of helium atoms are ionized, the electrical current in the glow region is mainly composed of electrons emitted from the cathode. The electrical resistance in this region can be written as, $$R_a = Edl/\Sigma ne\mu E \quad (10),$$

where E is the electrical field in the glow region, l the distance, n number of charge particles [electrons and (helium) ions], e the electron charge and μ the mobility of charge particles in this region. From this expression, resistance is related to the distance l of the separation between the pseudo-electrode and the anode, but inversely proportional to the number of fast moving electrons.

As trace impurities are introduced into the helium gas flow and are transported into the glow discharge region, their molecules are ionized by the high-energy electrons in the dark space or by the ionized helium ions through energy transfer. Since these molecules have different ionization cross-sections, ionization potential, different mobility and molecular mean free paths, their ions will modify the characters of the pseudo-electrode and cause a shift of the voltage drop $V_a$ through the dark space. The variation of the number of additional free electrons due to ionization of the impurities will cause a change in the electrical resistance $R_a$ in the glow region. These two effects caused by trace impurity elements are independent, and can be studied separately. In glow discharge detectors with a small separation gap (within one millimeter) between the cathode and anode, the effect of the change in the electrical resistance is quite small in comparing with the external resistance and can, therefore, be neglected. Two different kinds of glow discharge detectors were tested—one with small separation gap and the other with large separation gap—to separately study these two different effects.

Figure 5:
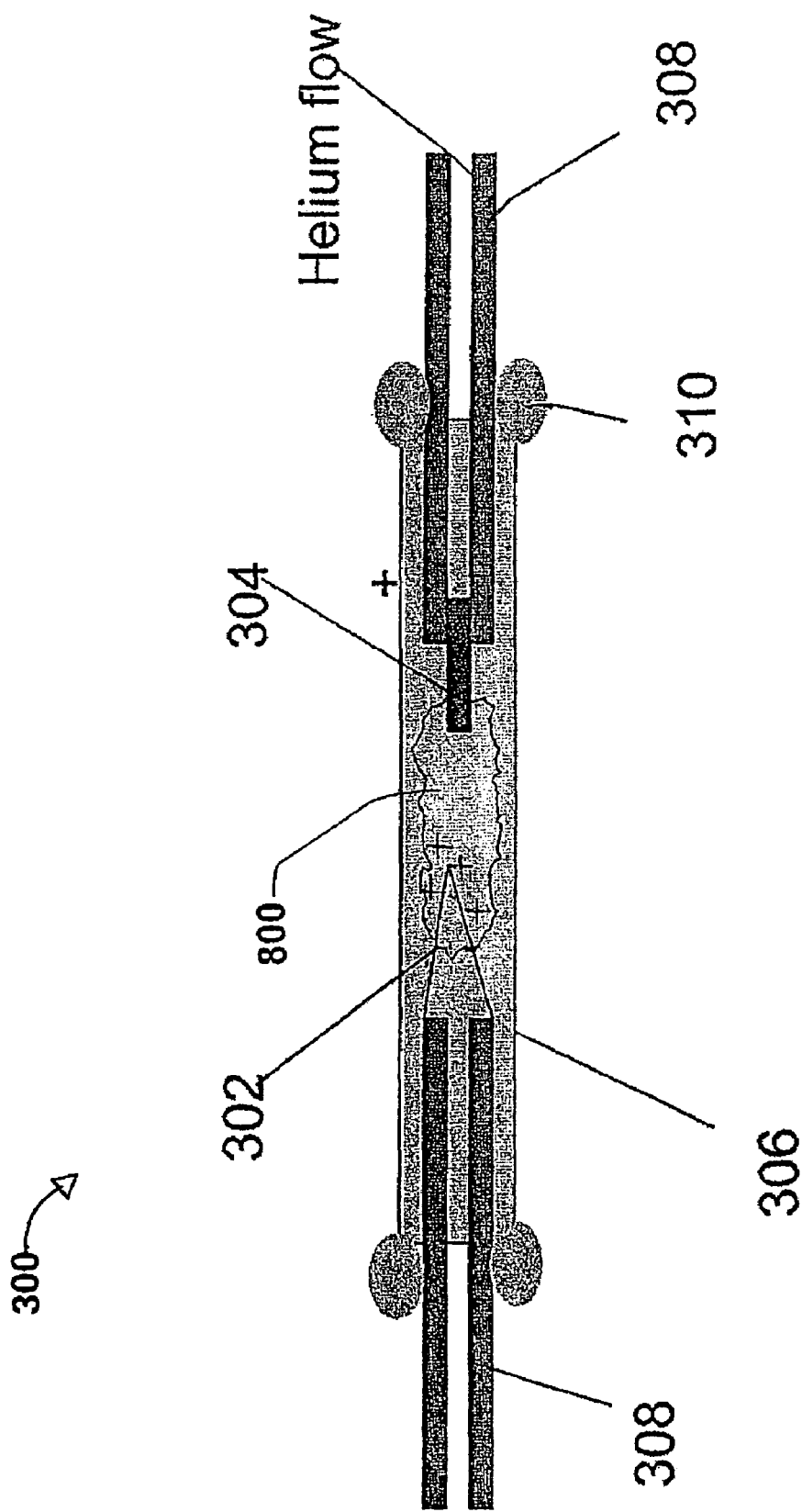
FIG. 5 is a cross sectional view of the glow discharge detector in the hand-held, real time detection gas chromatograph of FIGS. 1A and 1B.
Figure 5A:
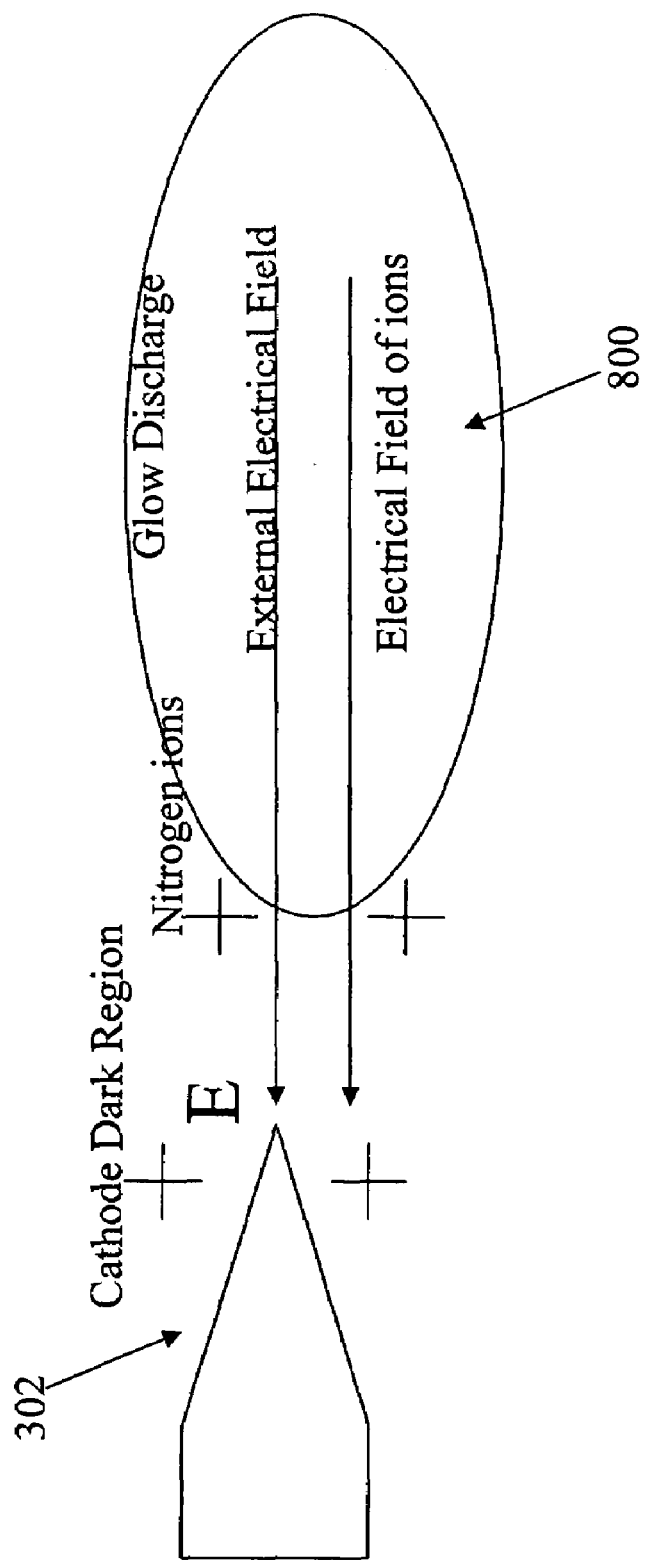
FIG. 5A is an enlarged cross-sectional view of the glow discharge detector of FIG. 5, illustrating the cathode dark region around the cathode, the positive ions, and the glow discharge region 800 or plasma between the electrodes.
Figure 7:
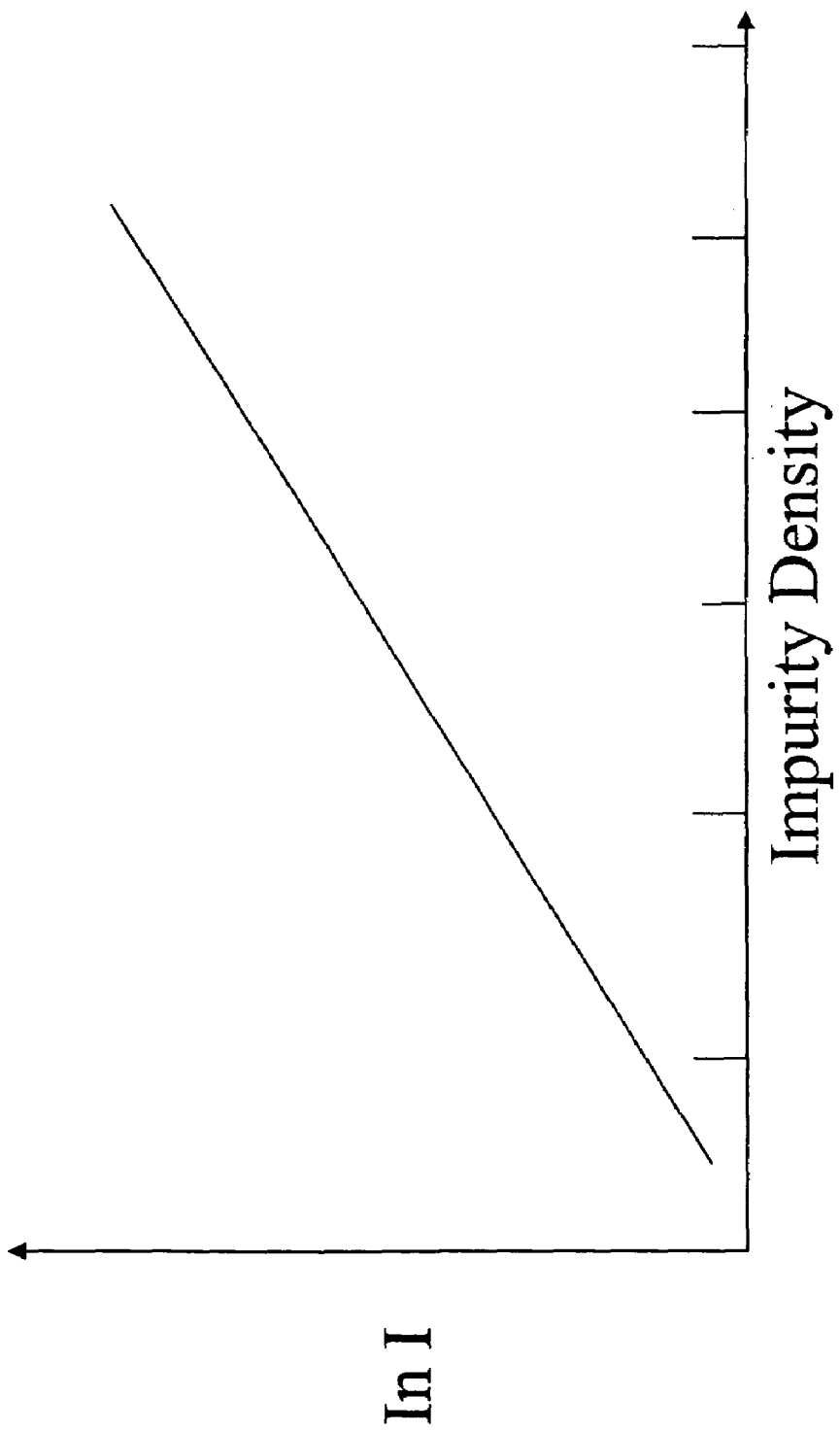
FIG. 7 is a graph illustrating voltage shift of the glow discharge detector of FIG. 5 as a function of quantity of impurities and variation of the electrical current.

For helium carrier gas, in a glow discharge detector 300 with a small separation gap, FIG. 5, the shift of the voltage drop $V_a$ due to trace elements is positive (increasing the voltage drop in the dark space) for all molecules with strong electron affinity, and is negative (decreasing the voltage drop in the dark space) for nearly all molecules without electron affinity (except a few molecules, like benzene, where a small positive shift is observed at parts per million concentration level.) In experimental measurements, this voltage shift is shown to be proportional to the quantity of the impurities, or, logarithmically with the variation of the electrical current. The sensitivity for molecules with strong electron affinity is about parts per trillion; the sensitivity for molecules without electron affinity is around parts per billion. This relationship is illustrated in FIG. 7.

In the glow region between the electrodes, 302 and 304, of the glow discharge detector 300, FIG. 5, molecules with strong electron affinity attach themselves with fast moving electrons and become negative ions. This effect reduces the number of free electrons in the glow region and, therefore, increases its resistance $R_a$ in the glow region 800, FIG. 5A. As previously demonstrated, total voltage across the glow region 800 of the detector 300 is also increased. On the other hand, the ionization of molecules without electron affinity increases the number of free electrons while decreasing the total voltage cross the glow region 800 of the detector 300. The two effects, the shift of voltage $V_a$ due to the positive ions of the impurities and the variation of the voltage over the glow region 800 due to change of the negative electrons, are in the same direction on the voltage drop cross the glow discharge detector 300 and, therefore, can be readily added together to increase the detection sensitivity (except for very few special molecules).

The preferred method for analyzing materials according to the present invention for a hand held, self-contained gas chromatograph system 10 begins with concentrating the sample (pre-concentrator 120) prior to introduction into the analytical separation column 200 with the sample of the compounds to be analyzed. The sample compounds are then transferred into the analytical separation column 200 using a transfer gas. Next, a carrier gas is passed inside the analytical separation column 200 for time separation of the sample compounds. The analytical separation column temperature then is controlled to achieve separation of the sample compounds. Vaporized sample compounds eluted from the analytical separation column are transferred to a glow discharge detector 300 to analyze the vaporized sample compounds. The electrical output of the vaporized sample from the glow discharge detector 300 is finally analyzed. Within this method, the transfer gas, the carrier gas, and gasses required for operation of the glow discharge detector 300 vaporized sample compounds are inert.

Figure 8:
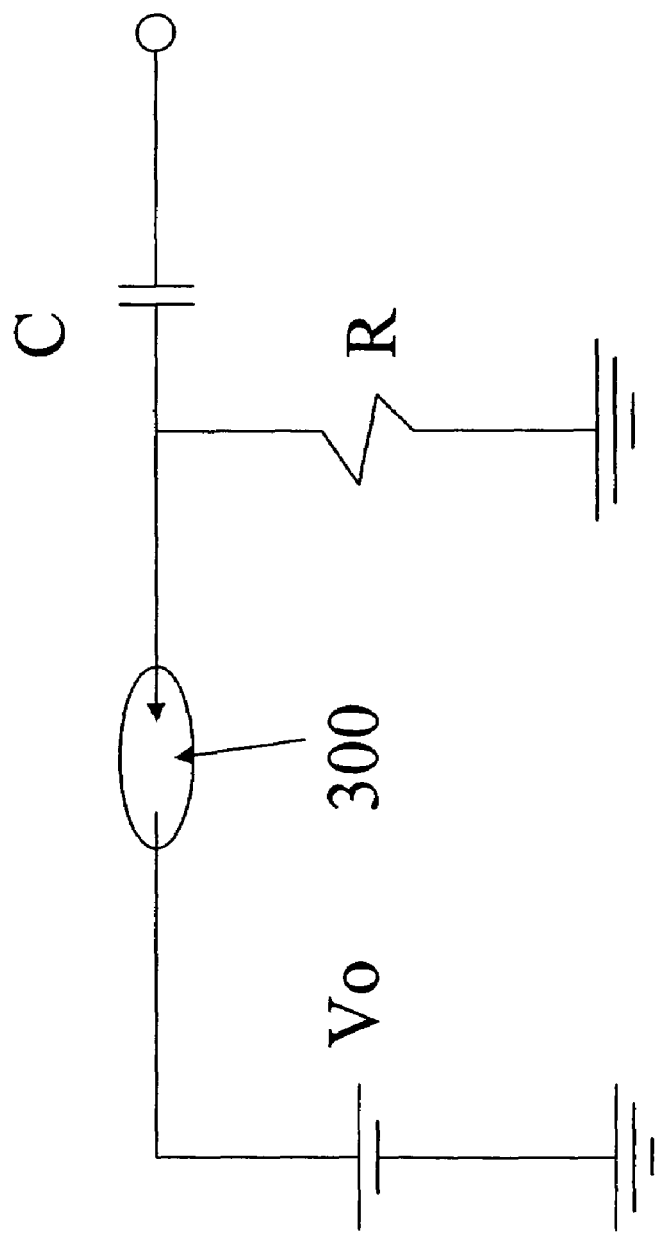
FIG. 8 is a representative circuit diagram for an embodiment to measure the impurity signal of the glow discharge detector of FIG. 5.

An electronic signal from the impurity is obtained either through a capacitor as illustrated in FIG. 8, or by a balance circuit, such as a four way bridge network.

Figure 9:
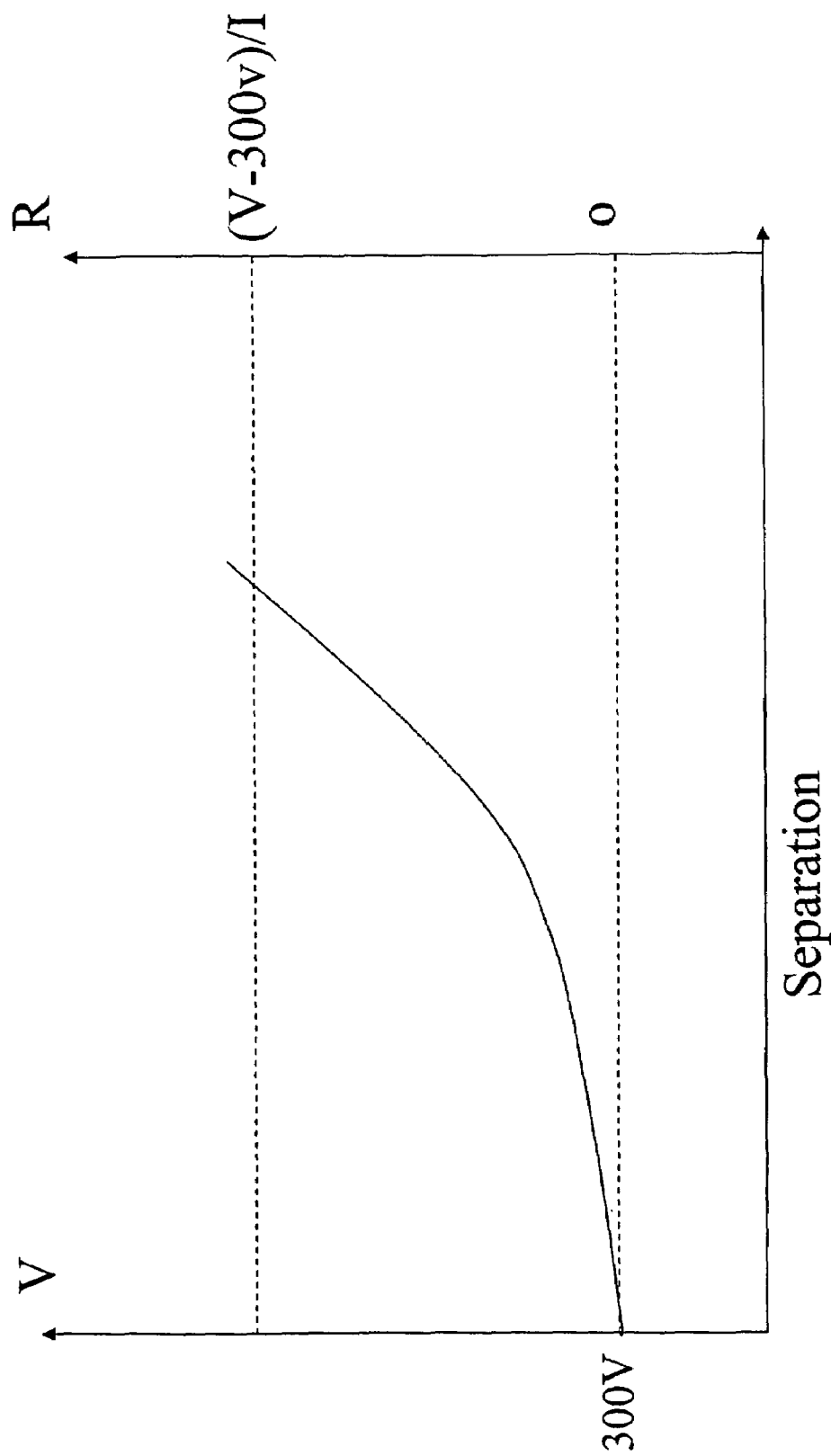
FIG. 9 is a graph illustrating the experimental measured data on an embodiment of the present invention with the internal resistance in a glow discharge detector of FIG. 5 in helium carrier gas.

In these cases, the relation for the detectable signal S for the impurity is derived from equation (2), as, $$S = \text{variation of } (V_o - V_a) * R_o / (R_o + R_a) \quad (11),$$

where $R_o$ is the external resistance. By substituting equation (10) into equation (11), and adding a variation of electronic density, the signal due to the change of the internal resistance of the glow discharge 800 is also linearly proportional to the quantity of the impurity in the first order approximation (when the number of the ionized trace elements is much smaller than the free electrons). From equation (11), there is a maximum of the impurity signal when the internal resistance $R_a$ equals to the external resistance $R_o$. FIG. 9 illustrates the experimental measured data on an embodiment of the present invention with the internal resistance of a glow discharge detector 300 in helium carrier gas. In that case, a three-watt external power supply of 3000 volts is provided. The embodiment of the present invention used to generate the data for FIG. 9 uses an external resistance of about 1.5 mega-ohms with about 1 cm separation between the cathode 302 element and the anode 304 element of the glow discharge detector 300 (the internal resistance is about 1.5 mega-ohms), FIG. 5. The estimated-current is about 0.9 mega-amps.

From testing embodiments of the present invention, it has been found that the most stable glow discharge is between a pointed cathode 302 and an anode 304 with flat plate front surface, FIG. 5. To contain the helium gas flow between them, these two electrodes are enclosed within glass tubing 306. The shape and the size of its container will certainly influence the electric field and electron flow and cause different distribution of the electrical resistance in the glow region. However, as long as the distribution is stable, the tested embodiments of the present invention suffice as a discharge detector. Therefore, the preferred embodiment of the present invention presents a structure with the simplest features. As illustrated in FIG. 5, two tungsten electrodes, 302 and 304, are first mounted inside two separated stainless steel tubes 308 and fixed in it by clinching part of the stainless steel tubes 308 onto each respective electrode. These two electrodes, 302 and 304, in the stainless steel tubes 308 are then mounted into a glass tube 306. The anode, 304, comprises a flat plate front surface. Once, the distance between the two electrodes is fixed, a very-low vapor pressure epoxy 310 is used to seal the stainless tubes to the glass tube. The embodiment of the apparatus of the present invention depicted in FIG. 5 provides a glow discharge detector maximized in its detection sensitivity under a particular carrier gas. A gas connector is used to connect a gas chromatography output on the right side of the stainless tube. The electrical connections are connected directly onto the two stainless tubes. The detector 300 uses a direct current (DC), constant wave detector controlled through a biased resistor, and a floating pseudo-electrode wherein the large variation of electron density due to trace amounts of impurities can be directly measured.

While the preferred embodiment of the present invention uses tungsten electrodes, 302 and 304, and stainless steel tubes, 308, these components can be made of metals with low work functions such as tungsten or molybdenum, and the like, or normal metals such as silver, copper or gold which would not be poisoned by oxygen to achieve a more stable system.

Figure 10:
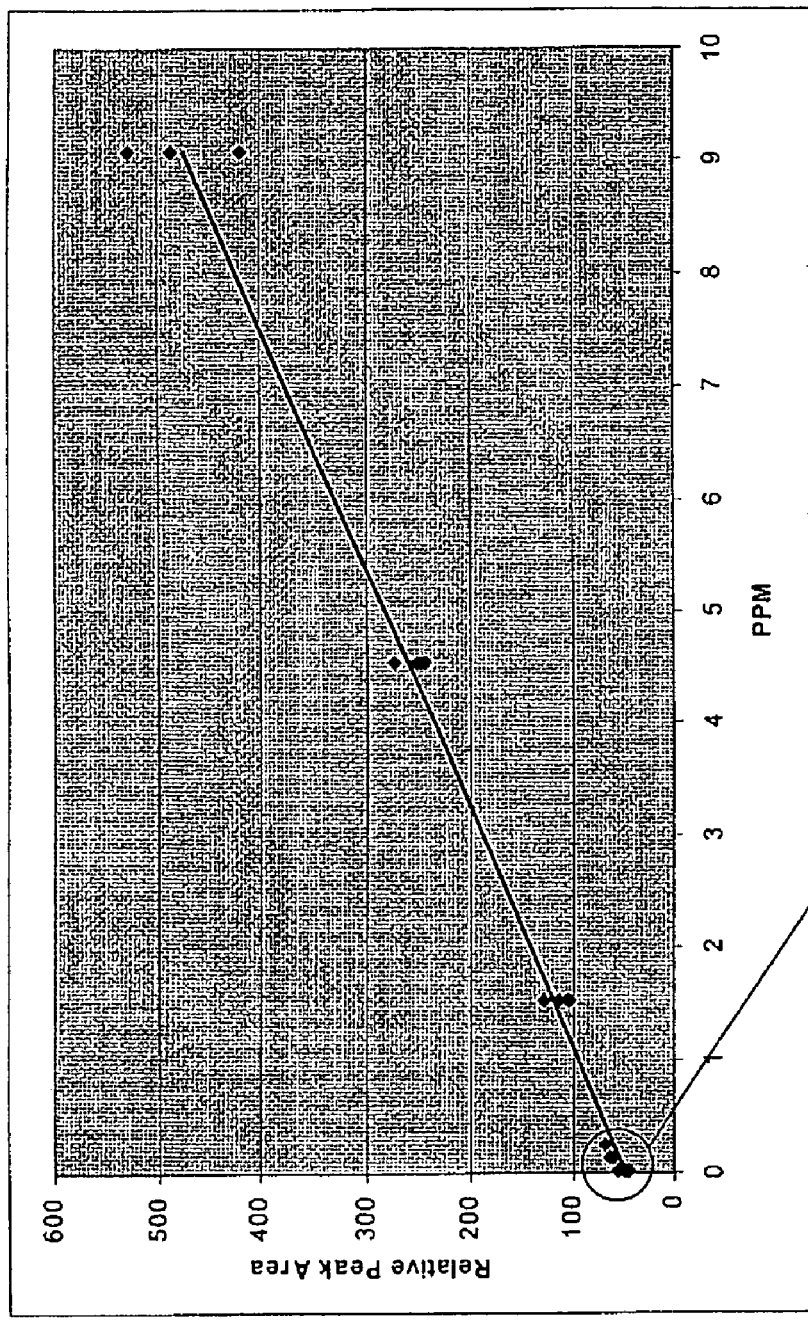
FIG. 10 is charted Gaussian peak height plotted against C5 sample concentration for an embodiment of glow discharge detector of FIG. 5 for sample concentrations ranging from less than one part per million to nine parts per million.
Figure 11:
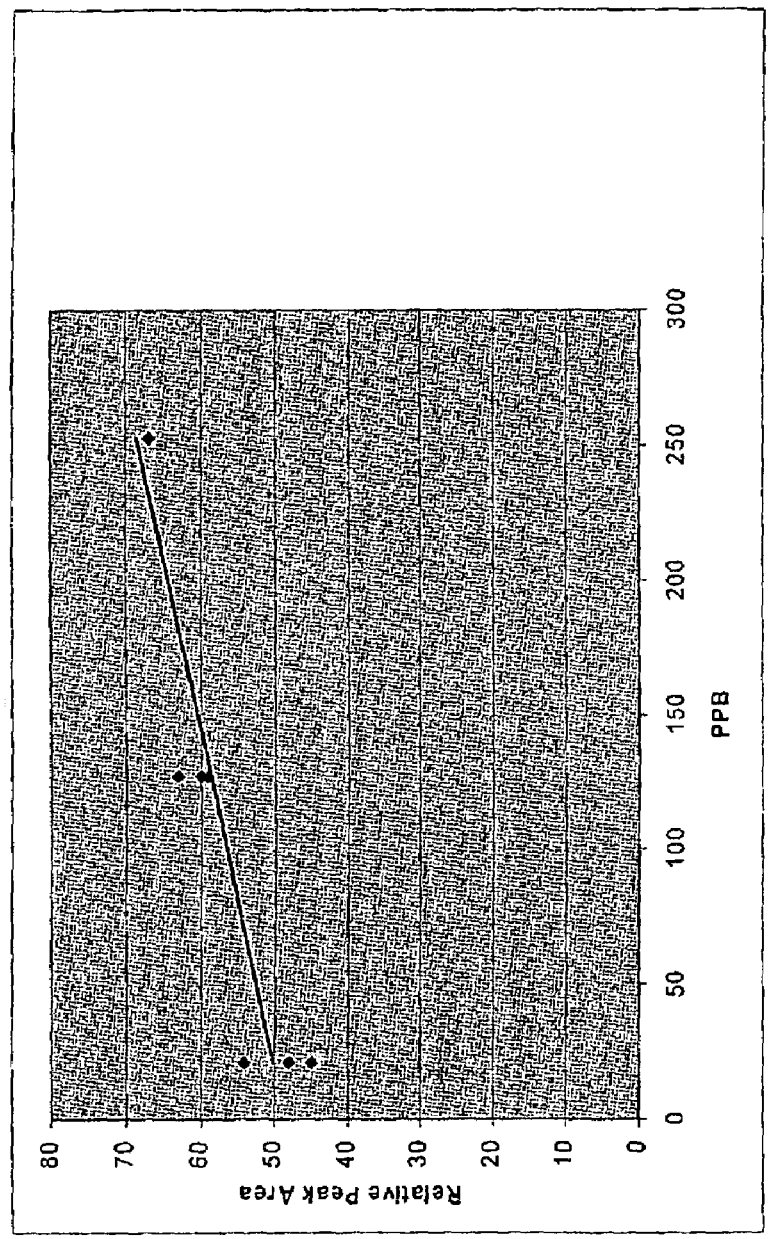
FIG. 11 is charted Gaussian peak height plotted against sample concentration for an embodiment of glow discharge detector of FIG. 5 for that range of sample concentrations from FIG. 10 ranging from less than 50 parts per billion to approximately 250 parts per billion.
Figure 12:
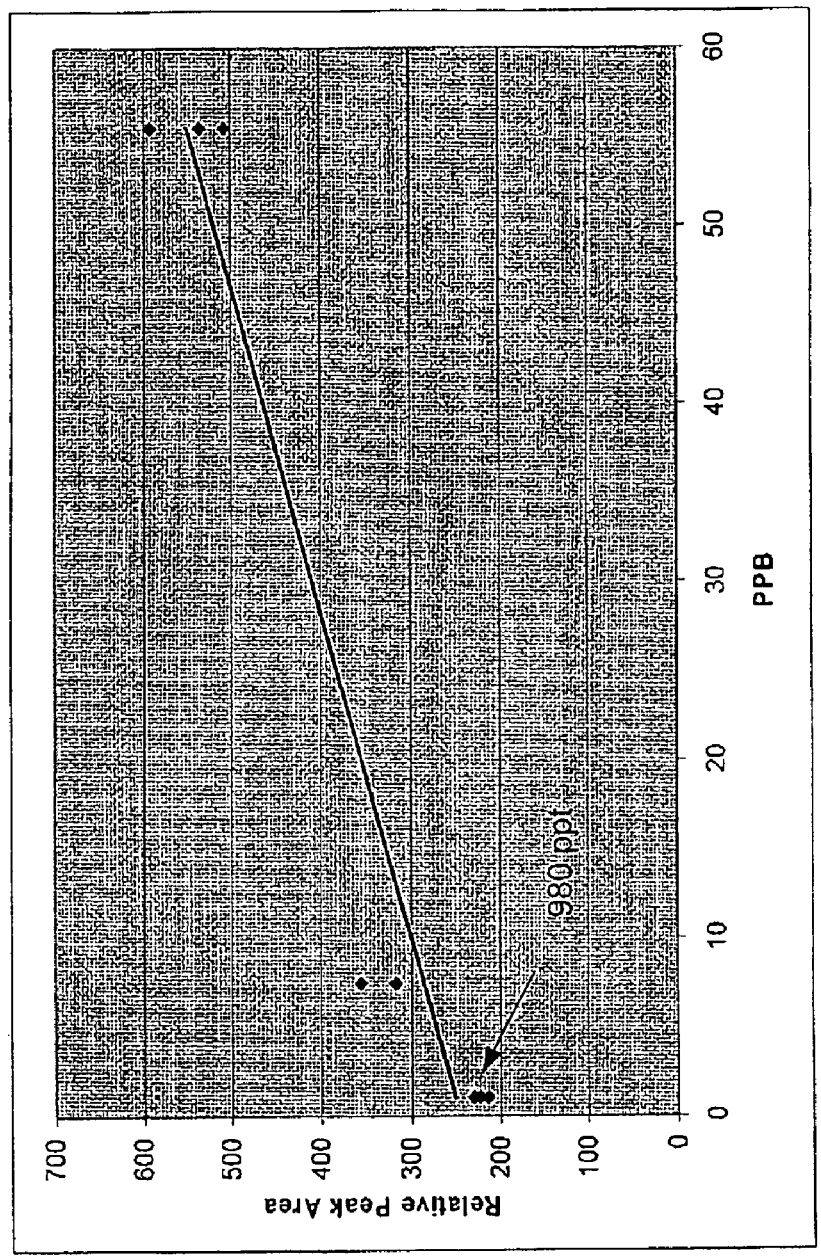
FIG. 12 is charted Gaussian peak area plotted against ethylene sample concentration for an embodiment of glow discharge detector of FIG. 5 for sample concentrations ranging from 980 parts per trillion to approximately 55 parts per billion.

With the glow discharge detector 300 connected in series with a silica capillary separation column 200, carrier gas (helium) purges from the injector port through the column and towards the glow discharge detector 300. Various concentrations of $C_2$ to $C_6$ hydrocarbon mixtures (from 50 ppm to 2.0 ppb in Helium) were injected into the system and the flow through the sample column is separated into small plugs. These sample plugs are transported by the carrier gas towards the glow discharge detector 300. The voltage change on the glow discharge detector 300 is measured. The measured voltage is plotted against the sample peak area. The signal detected by the present invention over concentration ranges from parts per trillion to parts per million remains positive in amplitude. Further, the glow discharge detector 300 of the present invention solves the problem of differential peaks by yielding measurement results in Gaussian peaks. FIGS. 10-12 depict the plot of Gaussian peak area against concentration. The present invention remains stable in the detection range of about 980 parts per trillion to nine parts per million, a change of sample concentration in beyond the order of six magnitudes.

An additional advantage of the flat plate anode 304 of the preferred embodiment of the present invention is that it allows a greater distance between discharge detector electrodes, 302 and 304. This increased distance provides a greater plasma area 800 which yields higher discharge stability. Higher externally applied voltage is also possible, yielding correspondingly higher measurements of the voltage drop across the cathode dark region, FIGS. 5A and 6. The increased applied voltage levels allow for faster flow rates and increased glow discharge sensitivity. Under the improvements of the preferred embodiment of the present invention, $C_2$ to $C_6$ hydrocarbon mixtures are analyzed in approximately forty seconds, as opposed to the one to two minute requirements of other systems.

The system, method, and apparatus of the present invention are suitably controlled through external interface hardware and software. In such remote function, the apparatus, method and system of the present invention can be coupled to user external devices including LCD display, keyboard, printers, modems, microprocessors, and other means. Input signals to control valve positions, heater controls, temperature, and timing parameters associated with each cycle of the chromatograph can be directed by known communication means, including means for wireless transmission, from external user devices to the apparatus. Similarly, analysis from the glow discharge detector 300 can be directed by known communication means, including means for wireless transmission, to external user interface devices providing graphical display and printing of system analysis data.

Figure 13:
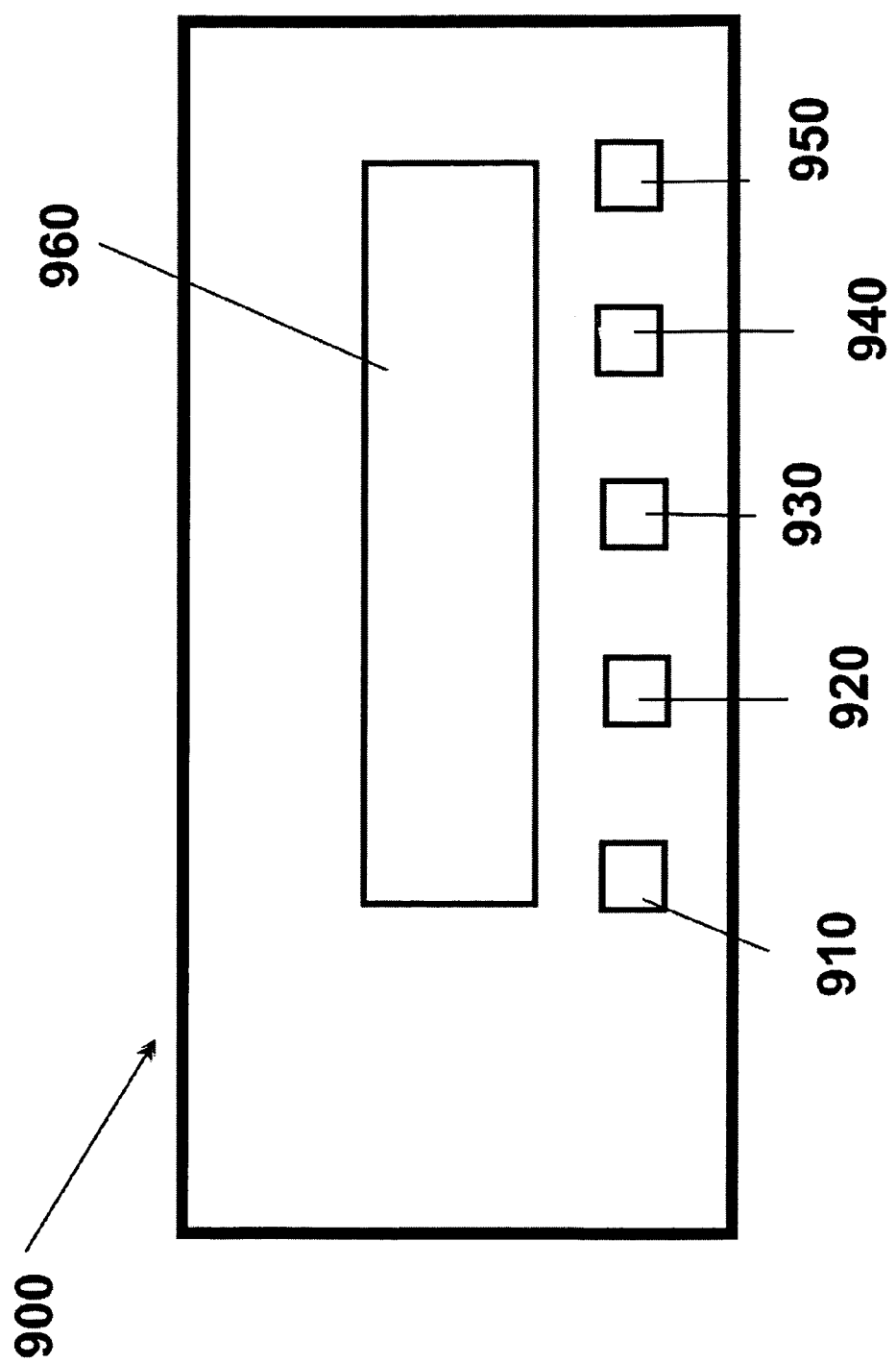

As depicted by the control panel 900 for an embodiment of the present invention, FIG. 13, user control functions provide for automatic sample selection 910, analysis 920, detector cleaning 930, detector calibration 940, termination of analysis 950, and an LCD display 960.

A hand-held, real time detection gas chromatograph, method, and system is thus provided depicting a highly sensitive, self-contained apparatus for trace impurity detection, particularly applicable where sample sizes are in nano- or sub-micro liter size.

The above description is included to illustrate the operation of the preferred embodiments and is not meant to limit the scope of the invention. The scope of the invention is to be limited only by the following claims. From the above discussion, many variations will be apparent to one skilled in the relevant art that would yet be encompassed the spirit and scope of the invention.

I claim:

1. A hand-held, real time gas chromatograph, comprising:
   hand-held, portable means for introducing a mobile phase including a sample gas in a carrier gas;

hand-held, portable means for concentrating and heating the mobile phase and carrier gas, the concentrating and heating means being mechanically connected to means for introducing the mobile phase;

hand-held, portable means for molecular separation of compounds mechanically connected to receive the concentrated and heated mobile phase; and hand-held, portable means for electronically analyzing the separated compounds mechanically connected to means for molecular separation of compounds, providing Gaussian peak analytical measurement.

2. The gas chromatograph of claim 1, wherein means for molecular separation comprises a silica capillary column having a uniform inside diameter and predetermined length.

3. The gas chromatograph of claim 2, further comprising an aluminum disk of uniform thickness and two sides, defining a central axis and having a spiral grooved channel of uniform diameter on each side sized to receive the column and defining a passage from one disk side to the other disk side near the central axis, such that the column enters the grooved channel on one disk side, spirals inwards towards the central axis within the grooved channel, passes to the other disk side within the grooved channel, spirals outwards from the central axis within the grooved channel, and exits the disk grooved channel on the other side.

4. The gas chromatograph of claim 3, further comprising means for high temperature conductivity covering the disk sides and securing the capillary column within the disk grooved channel.

5. The gas chromatograph of claim 4, further comprising means for controlling the temperature of the column to allow rapid column temperature ramping and cooling.

6. The gas chromatograph of claim 1, wherein the means for introducing a mobile phase including a sample gas in a carrier gas comprises at least one sample loop, a vacuum pump and at least one threeway valve mechanically connected to the pump, a sample gas port, a carrier gas port, and the means for concentrating and heating the mobile phase and carrier gas.

7. The gas chromatograph of claim 6, wherein at least one threeway valve and the vacuum pump operate to pull a sample into the sample pre-concentrator, and at least one three-way valve and the pressurized carrier gas flush the sample within the means for concentrating and heating the mobile phase and carrier gas, and release the adsorbed sample to the carrier gas stream into the means for molecular separation of compounds.

8. The gas chromatograph of claim 1, wherein the means for concentrating and heating the mobile phase and carrier gas comprises a nonconductive getter and resistance heater housed within glass tubing.

9. The gas chromatograph of claim 1, wherein the means for electronically analyzing the separated compounds comprises:
a direct current, constant wave glow discharge detector;
a solid rod anode having a flat end within the detector;
a tapering end cathode member located closely adjacent to the flat end of the solid rod anode, whereby the pointed cathode end defines a probe whereby variations of electron density due to trace amount of
impurities in the carrier gas can be directly measured; and
means for an electrical circuit comprising at least one power supply, at least one capacitor, and a plurality of resistors.

10. The gas chromatograph of claim 9, wherein the means for electronically analyzing the separated compounds further comprises:

a first annular member; and
a pair of annular members mounted in spaced relation in the first annular member wherein the solid rod anode having a flat end is mounted in one of the annular member pair and the solid rod cathode having a tapering end is mounted in the other annular member pair.

11. The gas chromatograph of claim 10, wherein the first annular member comprises a glass tube.

12. The gas chromatograph of claim 11, wherein the pair of annular members are composed of metals with low work functions selected from the group consisting of tungsten, molybdenum, silver, and gold.

13. The gas chromatograph of claim 12, wherein the anode and cathode are composed of metals with low work functions selected from the group consisting of tungsten, molybdenum, silver, and gold.

14. The gas chromatograph of claim 13, wherein the pair of annular members are mounted in the first annular member by a sealant.

15. The gas chromatograph of claim 14, wherein the sealant is composed of an epoxy.

16. The gas chromatograph of claim 15, wherein the tapering end of the cathode is tapered to a point, and wherein the point is located closely adjacent to the anode flat end.

17. The gas chromatograph of claim 16, wherein at least one capacitor is electrically connected intermediate a pair of resistors.

18. The gas chromatograph of claim 17, wherein the pair of resistors are each of a different size.

19. The gas chromatograph of claim 1, wherein the means for electronically analyzing the separated compounds comprises a direct current, constant wave glow discharge detector having solid rod anode and cathode members, the detector being controlled through a biased resistor.

20. The gas chromatograph of claim 19, wherein the glow discharge detector includes:
an outer annular tube composed of glass;
a pair of annular tubes mounted in spaced relation in the outer annular tube and composed of stainless steel;
the cathode member further composed of tungsten and having a pointed end mounted in one of the stainless steel tubes;
the anode member further composed of tungsten and having a flat end mounted in the other stainless steel tube in a manner whereby the cathode member pointed end is closely adjacent to the flat end.

21. The gas chromatograph of claim 20, wherein the anode and cathode members are mounted in the respective stainless steel tubes by at least one pinched area in the tube.

22. The gas chromatograph of claim 21, wherein the anode, cathode, and pair of annular tubes are each mounted coaxially in the outer annular tube.

23. The gas chromatograph of claim 22, wherein the pair of annular tubes are only partially located within the outer annular tube.

24. The gas chromatograph of claim 1, wherein the carrier gas is selected from the group consisting of nitrogen, hydrogen, helium, and argon.

25. A method for analyzing materials vaporizable in a hand-held, self-contained gas chromatograph system, the method comprising the steps of:
providing a hand-held, self-contained gas chromatograph system including hand-held means for concentrating a sample of compounds to be analyzed prior to introduction into an analytical separation column, hand-held analytical separation column means, hand-held means for controlling the temperature of the analytical separation column, and hand-held means for analyzing vaporized sample compounds eluted from the analytical separation column means presented in Gaussian peaks;

filling means for concentrating the sample prior to introduction into an analytical separation column with the sample of the compounds to be analyzed;

transferring the sample compounds into the analytical separation column means with a transfer gas;

passing a carrier gas inside the analytical separation column means for time separation of the sample compounds;

controlling the temperature of the analytical separation column means for achieving separation of the sample compounds;

transferring the vaporized sample compounds eluted from the analytical separation column means into the means for analyzing vaporized sample compounds; and analyzing the data output of the means for analyzing vaporized sample compounds, characterized in that the transfer gas, the carrier gas, and gasses required for operation of the means for analyzing vaporized sample compounds are inert.

26. The method of claim 25, whereby the data output comprises Gaussian peaks.

27. The method of claim 25, wherein the carrier gas is selected from the group consisting of nitrogen, hydrogen, helium, and argon.

28. The method of claim 25, further comprising the steps of:
 selecting a sample;
 calibrating the system;
 analyzing the sample;
 terminating the analysis; and
 cleaning the system.

29. The method of claim 28, further comprising the step of providing a user interface panel whereby the steps of sample selection, sample analysis, detector cleaning, detector calibration, and termination of analysis are automated.

30. The method of claim 25, whereby analyzing the data output includes graphical analysis of chromatography data by display and printing.

31. The method of claim 25, whereby the means for analyzing vaporized sample compounds comprises measuring the voltage drop between electrodes of a glow discharge detector.

32. A hand-held gas chromatograph system for analyzing vaporizable materials, the system comprising:
 hand-held means for filling a sample injection device with a sample of compounds to be analyzed;
 hand-held means for concentrating the sample;
 hand-held means for transferring the concentrated sample with a transfer gas into means for analytical separation column;
 hand-held means for passing a carrier gas inside the analytical separation column means for time separation of the sample compounds;
 hand-held means for controlling the temperature of the analytical separation column means;
 hand-held means for glow discharge detection of vaporized sample compounds eluted from the analytical separation column means;
 hand-held means for analyzing output from the glow discharge detection means for detecting vaporized sample compounds eluted from the analytical separation column means, whereby analytical measurements are provided by Gaussian peaks; and
characterized in that the transfer gas, the carrier gas, and the gasses required for the operation of means for glow discharge detection are inert.

33. The system according to claim 32, wherein the means for concentrating the sample consists of a sample preconcentrator element comprising flow through stainless steel inlet and outlet tubing, the stainless steel tubing being linked to a center section of glass tubing comprising means for resistant heating.

34. The system according to claim 32, wherein the analytical separation column means comprises a silica capillary column having a uniform inside diameter and predetermined length.

35. The system according to claim 34, further comprising an aluminum disk of uniform thickness and two disk sides, defining a central axis, and having a spiral grooved channel of uniform diameter on each side sized to receive the column and defining a passage from one disk side to the other near the central axis, such that the column enters the grooved channel on one disk side, spirals inwards towards the central axis within the grooved channel, passes to the other disk side within the groove passage, spirals outwards from the central axis within the grooved channel, and exits the disk grooved channel on the other side.

36. The system according to claim 34, wherein a high temperature heat conductive paste covers the disk sides and capillary column.

37. The system according to claim 36, wherein the means for controlling the temperature of the analytical separation column means allows rapid column temperature ramping and cooling and further comprises means for providing resistant flat heat to the disk and means for providing convective air flow to the disk.

38. The system according to claim 36, wherein the maximum operational temperature of the column is 350 degrees Celsius.

39. The system according to claim 38, wherein the glow discharge detection means for detecting vaporized sample compounds eluted from the analytical separation column means comprises:
 a direct current, constant wave glow discharge detector;
 a solid rod anode having a flat end within the detector; and
 a pointed end cathode member located closely adjacent to the flat end of the solid rod anode, whereby the pointed end defines a probe
 whereby variations of electron density due to trace amount of impurities in the carrier gas can be directly measured.

40. The system according to claim 32, wherein the glow discharge detection means for detecting vaporized sample compounds eluted from the analytical separation column means comprises:
 a first annular member;
 a pair of annular members mounted in co-axial spaced relation in the first annular member;
 a solid rod member having a tapering end mounted co-axially in one of the pair of annular members; and
 a solid rod having a flat end mounted co-axially in another of the pair of annular members with the flat end located closely to the solid rod member tapering end.

41. The system according to claim 40, wherein the first annular member comprises a glass tube.

42. The system according to claim 41, wherein the pair of annular members comprises a pair of tubes consisting of the same metal.

43. The system according to claim 42, further comprising an electrical circuit including a power supply, at least one capacitor, and a plurality of resistors.

44. The system according to claim 32, wherein the means for transferring the concentrated sample with a transfer gas into the analytical separation column means and the means for passing a carrier gas inside means for analytical separation column for time separation of the sample compounds comprises pressurized helium gas.

45. The system according to claim 32, wherein the means for concentrating the sample comprises glass tubing housing a nonconductive getter and means for resistance heating.

46. The system according to claim 45, further comprising a VICI conventional eight port valve.

47. The system according to claim 32, further comprising means to collect gas samples.

48. The system according to claim 47, wherein means to collect gas samples further comprises at least one sniffer.

49. The system according to claim 32, further comprising means to collect liquid samples.

50. The system according to claim 32, further comprising a user interface control panel to automate specific system functions.

51. The system according to claim 50, wherein the system functions comprise functions selected from the group consisting of sample selection, analysis, detector cleaning, detector calibration, termination of analysis, and LCD display.

52. The system according to claim 32, wherein all system components are contained within 624 cubic inches and total a weight of approximately twelve pounds.

* * * * *